(12) United States Patent
Ryu et al.

(10) Patent No.: US 7,062,309 B2
(45) Date of Patent: Jun. 13, 2006

(54) ELECTRODE-CONNECTOR PROTECTING CAP AND ELECTRODE-CONNECTOR INCLUDING THE SAME

(75) Inventors: Chang Yong Ryu, Daejeon-Shi (KR); Seung Hwan Kim, Daejeon-Shi (KR); Yun Tae Kim, Daejeon-Shi (KR)

(73) Assignee: Electronics and Telecommunications Research Institute, Daejon-Shi (KR)

( * ) Notice: Subject to any disclaimer, the term of this patent is extended or adjusted under 35 U.S.C. 154(b) by 162 days.

(21) Appl. No.: 10/784,978

(22) Filed: Feb. 25, 2004

(65) Prior Publication Data
US 2005/0137472 A1   Jun. 23, 2005

(30) Foreign Application Priority Data
Dec. 18, 2003   (KR) .................... 10-2003-0093142

(51) Int. Cl.
*A61B 5/04* (2006.01)
(52) U.S. Cl. .................... 600/372; 600/394
(58) Field of Classification Search ............... 600/372, 600/394
See application file for complete search history.

(56) References Cited

U.S. PATENT DOCUMENTS

| | | | |
|---|---|---|---|
| 4,331,153 A | | 5/1982 | Healy |
| 4,383,529 A | * | 5/1983 | Webster ................. 604/20 |
| 4,503,860 A | | 3/1985 | Sams et al. |
| 4,686,995 A | * | 8/1987 | Fournial et al. ............ 600/391 |
| 4,757,817 A | | 7/1988 | Healy |
| 4,773,424 A | * | 9/1988 | Inoue et al. ................. 600/394 |
| 5,355,883 A | | 10/1994 | Ascher |
| 5,978,693 A | | 11/1999 | Hamilton et al. |

* cited by examiner

*Primary Examiner*—Lee S. Cohen
(74) *Attorney, Agent, or Firm*—Meyer, Brown, Rowe & Maw LLP

(57) ABSTRACT

Provided is an electrode-connector protecting cap for ambulatory physiological signal measurement comprising a hemisphere cap, a wing positioned at a periphery of the hemisphere cap and having a contact surface connected to the electrode-connector; and an opening for a wire to be passed through and formed in the hemisphere cap, and an electrode-connector including the same, whereby a connection between the electrode and the connector can be protected and the noise occurrence can be prevented.

22 Claims, 4 Drawing Sheets

Top View  Bottom View

ELECTRODE-CONNECTOR PROTECTING CAP AND ELECTRODE-CONNECTOR INCLUDING THE SAME

BACKGROUND

1. Field of the Invention

The present invention relates to an ambulatory physiological signal measurement apparatus employing a disposable electrode such as 24 hr electrocardiogram monitor (e.g., ECG Holter monitor). In particular, the present invention relates to an electrode-connector used in the ambulatory physiological signal measurement apparatus, an electrode-connector protecting cap for preventing noise from being occurred due to external contact and impact, and an electrode-connector including the same.

2. Discussion of Related Art

An electrode is attached to a skin of a subject, which is connected to a physiological signal measurement apparatus through long wire to measure the physiological signal. In this case, the long wire causes motion artifacts in the physiological signal measurement apparatus. In addition, when the long wire is pulled, impedance between the skin of the subject and the metal electrode is changed, which causes noise-mixed signals in the physiological signal measurement apparatus.

Various approaches have been proposed to solve the above-mentioned problems. S. Pat. No. 5,978,693 entitled "apparatus and method for reduction of motion artifact" to Patrick S. Hamilton, Michael G. Curley, and Roberto M. Aimi, (issued in 1999) teaches a method that attaches a strain gauge to a foam pad and detects separate motion artifacts to thereby reduce the motion artifacts from its original signal.

Other method for reducing the motion artifact has been disclosed in U.S. Pat. No. 4,757,817 to James W. Healy. In this method, some portions of a foam pad on which a rectangular disposable electrode is placed are cut to place a connector wire between the some portions, so that it can be securely held. The wire and the electrode may be securely held, however, electrode-connecter portion is exposed, so that it may cause noise when direct contact or impact is applied to the electrode-connecter portion.

Another method has been disclosed in U.S. Pat. No. 4,503,860 to Marvin W. Sams, and Samuel L. Wasson. This method discloses an anchoring pad below an electrode to prevent electrode and connector wire from being moved. The anchoring pad acts to be securely attached to a skin of a subject by making the bottom surface of the anchoring pad flat and sticky. The electrode-connecter portion is also exposed, so that it may cause noise when direct contact or impact is applied to the electrode-connecter portion.

Above-mentioned methods have improved a motion artifact removal effect a little, however, when they are applied to an apparatus such as an ambulatory physiological signal measurement apparatus that can be attached to a body, the noise occurred from stimulus or impact due to a contact between the electrode and the connector can not be reduced. Furthermore, most of the related arts should design or make a new electrode, which causes an additional cost and inconvenience.

SUMMARY OF THE INVENTION

The present invention is directed to an electrode-connector, an electrode-connector protecting cap for ambulatory physiological signal measurement capable of securely holding wire and preventing noise due to external stimulus contact and impact, and an electrode-connector including the same.

To achieve the above purpose, one aspect of the present invention is to provide an electrode-connector protecting cap, comprising: a hemisphere cap; a wing positioned at a periphery of the hemisphere cap and having a contact surface connected to the electrode-connector; and an opening for wire to be passed through and formed in the hemisphere cap.

Here, the hemisphere cap is formed by a transparent plastic. The wing further comprises adhesive to be connected to the hemisphere cap, consists of three portions with 120° spaced from one another, is of a loop shape, and has a groove. In addition, the opening is positioned at the periphery of the hemisphere cap.

In a preferred embodiment of the present invention, the electrode connector further comprises a tube through which the wire is passed, and contacted around the opening of the hemisphere cap. The tube is of an arch shape, and has a wire fixing portion that can securely hold the wire. Here the wire fixing portion is of a protruded shape.

Another aspect of the present invention is to provide an electrode-connector for ambulatory physiological signal measurement, comprising: an electrode-connector having an electrode, a wire, a foam pad surrounding sides of the electrode, an electrode connecting portion taking one of a protruded shape and a recessed shape and electrically connected to the electrode, and a connector taking the other and electrically connected to the wire; and an electrode-connector protecting cap of the present invention.

DETAILED DESCRIPTION OF PREFERRED EMBODIMENTS

Hereinafter, embodiments of the present invention will be described with reference to accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
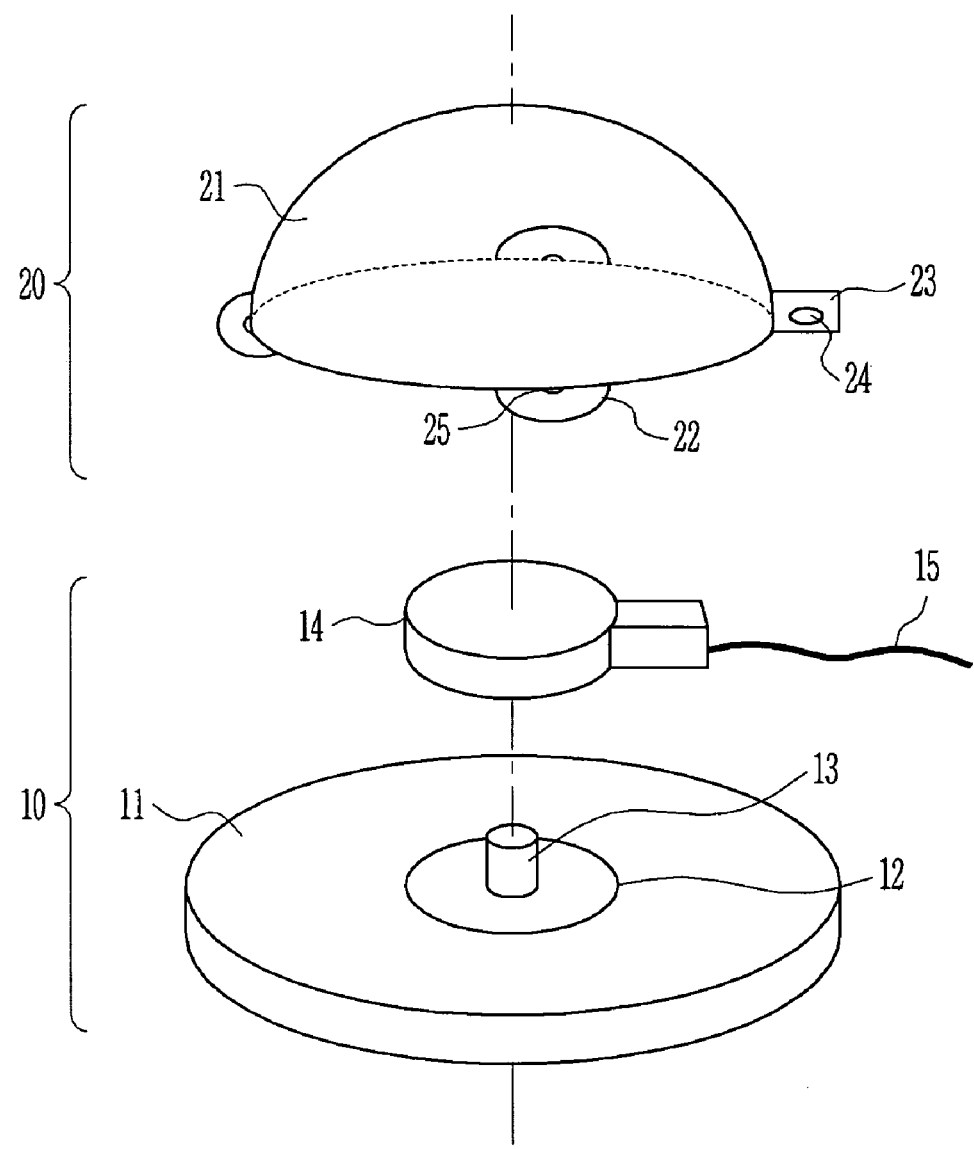
FIGS. 1 to 3 show perspective, side and plan views of an electrode-connector for ambulatory physiological signal measurement including an electrode-connector protecting cap in accordance with a first embodiment of the present invention, respectively.
Figure 2:
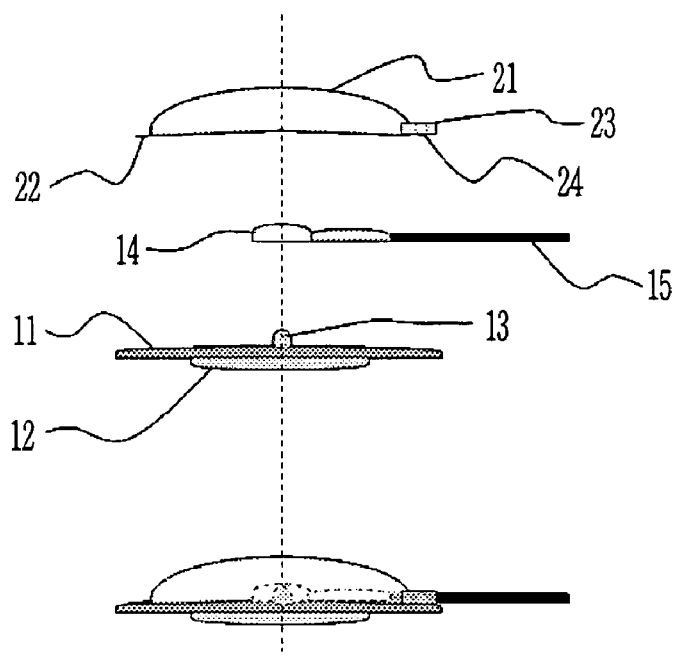
Figure 3:
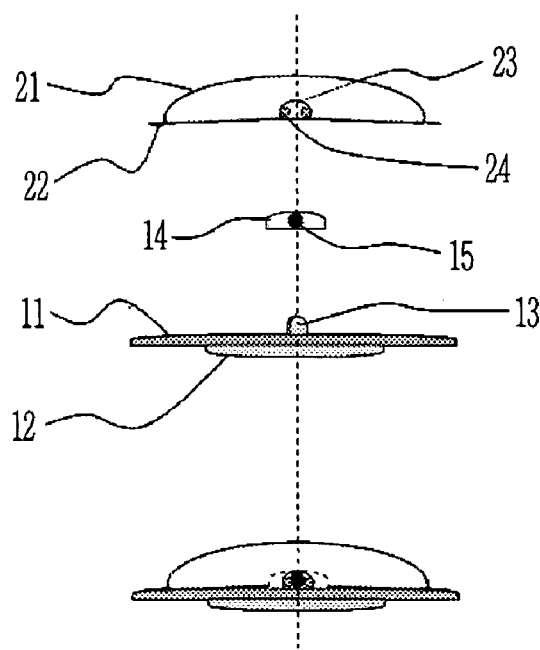

FIGS. 1 to 3 show perspective, side and plan views of an electrode-connector for ambulatory physiological signal measurement including an electrode-connector protecting cap in accordance with a first embodiment of the present invention, respectively.

An electrode-connector for ambulatory physiological signal measurement including a protecting cap in FIGS. 1 to 3 includes an electrode-connector 10 and an electrode-connector protecting cap 20.

The electrode-connector 10 comprises a foam pad 11 with an adhesive for skin attachment, an electrode 12 for ambulatory signal measurement with a conductive gel applied on a bottom surface thereof to reduce impedance between the skin and the electrode, a connector end 13 for connecting the electrode to a connector, a connector 14 connected to the connector end 13, and a wire 15 connected to an apparatus for measuring physiological signal. The foam pad 11, the electrode 12, and the connector end 13 may be referred to as a disposable electrode all together.

The electrode-connector protecting cap 20 consists of a transparent and plastic hemisphere cap 21 for protecting an electrode-connector connecting portion from an external impact, wings 22 having adhesive applied on its bottom surface and attached to the foam pad 11, and a tube 23 through which the connector wire is passed. A wire fixing portion 24 is positioned inside the tube 23 to securely hold the connector wire, and a groove 25 is formed within the wings 22 to prevent air from being trapped. The wings 22 may be of various shapes and can consist of three portions with 120° spaced from one another as shown in FIG. 1, and also may have a shape of one loop. An opening should be formed where the tube 23 of the hemisphere cap is placed to have the connector wire passed through. Furthermore, it is advantageous for the fabrication that the opening is formed at the periphery of the hemisphere cap 21, which means that the hemisphere cap 21 is placed above an upper portion of the opening, and the lower portion of the opening is opened before it is connected to the electrode-connector 10 and contacted with the foam pad 11 after it is connected to the electrode-connector 10. When the opening is formed at the periphery, the tube 23 is preferably of an arch shape where the lower portion thereof is opened before it is connected to the electrode-connector 10.

Figure 4:
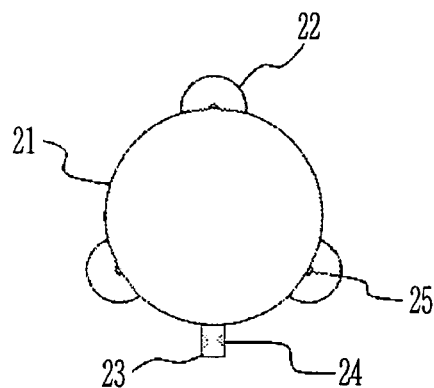
FIG. 4 shows the electrode-connector protecting cap viewed from its top and bottom positions in accordance with the first embodiment of the present invention.
Figure 4:
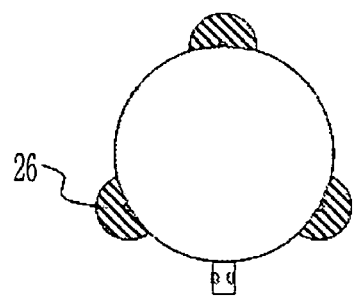

FIG. 4 shows the electrode-connector protecting cap viewed from its top and bottom positions in accordance with the first embodiment of the present invention. In FIG. 4, the electrode-connector protecting cap comprises the hemisphere cap 21, the wings 22, the tube 23, the wire fixing portion 24, and the groove 25, wherein adhesive 26 are applied on the wings 22 to be contacted with the foam pad 11.

Figure 5:
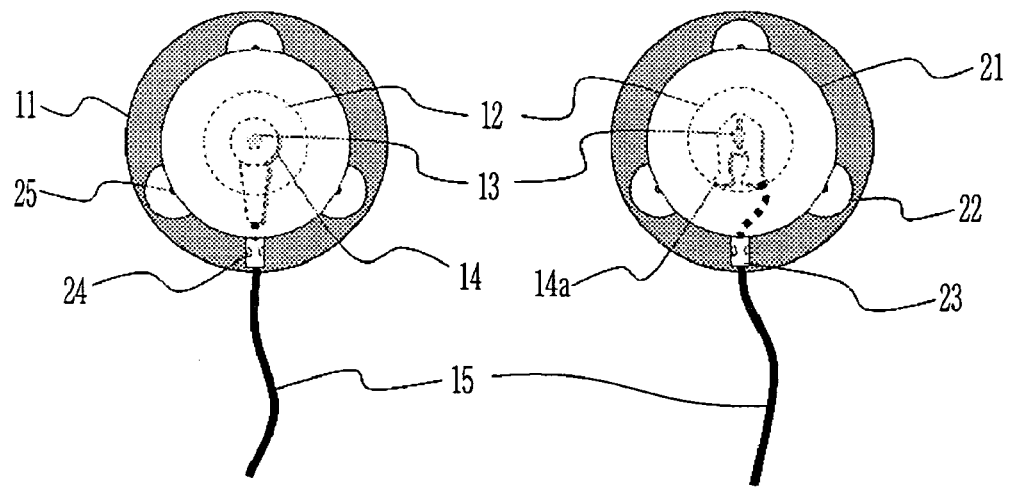
FIG. 5 shows the electrode-connector for ambulatory physiological signal measurement including the electrode-connector protecting cap viewed from its top position in accordance with the first embodiment of the present invention.

FIG. 5 shows the electrode-connector for ambulatory physiological signal measurement including the electrode-connector protecting cap viewed from its top position in accordance with the first embodiment of the present invention. In FIG. 5, the electrode-connector for ambulatory physiological signal measurement including the protecting cap comprises the foam pad 11, the electrode 12, the electrode connecting portion 13, the connector 14, the wire 15, the hemisphere cap 21, the wings 22, the tube 23, the wire fixing portion 24, and the groove 25. Alternatively, the electrode-connector for ambulatory physiological signal measurement including the electrode-connector protecting cap may include any other type of connector such as a connector 14a.

Figure 6:
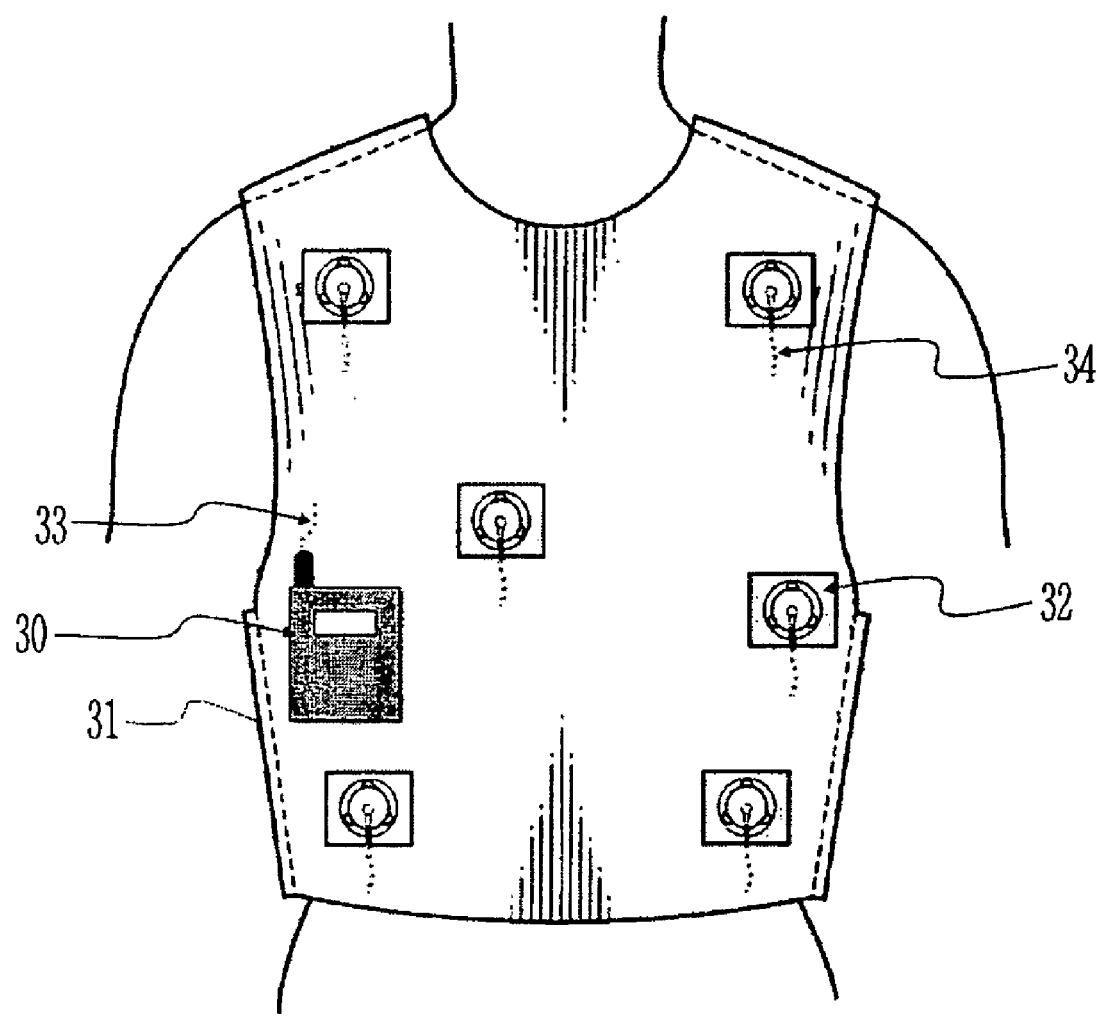
FIG. 6 shows an example when the present invention is applied in an ambulatory physiological signal measurement apparatus.

FIG. 6 shows an example when the present invention is applied in an ambulatory physiological signal measurement apparatus. In FIG. 6, a numerical reference 30 indicates an ambulatory physiological signal measuring apparatus, and a numerical reference 31 indicates the ambulatory physiological signal measuring apparatus including shirts. The ambulatory physiological signal measuring apparatus may amplify signals obtained from the ambulatory physiological signal measuring electrode-connector including the protecting cap to store them in its own memory, or transmit them to a computer by using Bluetooth, wireless internet, or public radio network. A numerical reference 32 indicates a window for attaching the ambulatory physiological signal measuring electrode-connector including the protecting cap to skin of a subject, a numerical reference 33 indicates a wire connected from the physiological signal measuring electrode-connector including the protecting cap through inside of the shirts to the ambulatory physiological signal measuring apparatus 30, and a numerical reference 34 indicates a wire connected from the ambulatory physiological signal measuring electrode-connector including the protecting cap to the inside of the shirts. In general, the ambulatory physiological signal measuring apparatus 30 and the ambulatory physiological signal measuring electrode-connector including the protecting cap are attached to the subject who has put on shirts 31. In this case, the subject may move with shirts on, so that the electrode-connector is inevitably contacted with the shirts to thereby cause noise. However, the shirts and the electrode-connector are not contacted in accordance with the present invention, which results in reduced noise.

The present invention can be applied for protecting an apparatus that is sensitive to external contact or stimulus even when other device such as a strain gauge is disposed in the electrode-connector. In addition, contacts due to clothes can be removed to measure accurate moving artifact when an accelerometer sensor is equipped in the electrode-connector to reduce the moving artifact. Other devices equipped in the electrode-connector may also be protected in accordance with the present invention. In addition, the present invention can be applied to any ambulatory physiological signal measurement apparatuses using a disposable electrode.

It is advantageous that the electrode-connector protecting cap for ambulatory physiological signal measurement and the electrode-connector including the same can protect a connection between the electrode and the connector in accordance with the present invention.

Furthermore, it is advantageous that the electrode-connector protecting cap for ambulatory physiological signal measurement and the electrode-connector including the same in accordance with the present invention can prevent noise from being occurred due to movement contact between clothes and the electrode-connector when the subject has the ambulatory physiological signal measurement apparatus attached and then put on clothes.

In addition, the electrode-connector protecting cap for ambulatory physiological signal measurement and the electrode-connector including the same in accordance with the present invention uses a disposable transparent cap to thereby implement convenient use and low cost.

In addition, the electrode-connector protecting cap for ambulatory physiological signal measurement and the electrode-connector including the same in accordance with the present invention has a portion for fixing the wire connected to the connector, so that the noise delivery due to the wire movement can be reduced.

In addition, the electrode-connector protecting cap for ambulatory physiological signal measurement and the electrode-connector including the same in accordance with the present invention can use the conventional connector wire.

In addition, the electrode-connector protecting cap for ambulatory physiological signal measurement and the electrode-connector including the same in accordance with the present invention can be attached onto the electrode in a cap form, so that it can act as a buffer against an external impact.

In addition, the electrode-connector protecting cap for ambulatory physiological signal measurement and the electrode-connector including the same in accordance with the present invention does not require an additional circuit or device to thereby implement noise removal with a low cost.

In addition, the electrode-connector protecting cap for ambulatory physiological signal measurement and the electrode-connector including the same in accordance with the present invention can fix the wire at desired directions using the tube and the wire fixing portion.

Having described specific preferred embodiments of the invention with reference to the accompanying drawings, it will be appreciated that the present invention is not limited to those precise embodiments, and that various changes and modifications can be effected therein by one of ordinary skill in the art without departing from the scope of the invention as defined by the appended claims.

What is claimed is:

1. An electrode-connector protecting cap, comprising:
   a hemisphere cap;
   a wing positioned at a periphery of the hemisphere cap and having a contact surface adapted to be connected to an electrode-connector; and
   an opening for a wire to be passed through and formed in the hemisphere cap.

2. The electrode-connector protecting cap as claimed in claim 1, wherein the hemisphere cap is formed by a transparent plastic.

3. The electrode-connector protecting cap as claimed in claim 1, wherein the wing further comprises adhesive for connecting the wing to the electrode-connector.

4. The electrode-connector protecting cap as claimed in claim 1, wherein the wing consists of three portions with 120° spaced from one another.

5. The electrode-connector protecting cap as claimed in claim 1, wherein the wing is of a loop shape.

6. The electrode-connector protecting cap as claimed in claim 1, wherein the wing has a groove.

7. The electrode-connector protecting cap as claimed in claim 1, wherein the opening is positioned at the periphery of the hemisphere cap.

8. The electrode-connector protecting cap as claimed in claim 1, further comprising a tube through which the wire is passed, and contacted around the opening of the hemisphere cap.

9. The electrode-connector protecting cap as claimed in claim 8, wherein the tube is of an arch shape.

10. The electrode-connector protecting cap as claimed in claim 8, wherein the tube has a wire fixing portion that can securely hold the wire.

11. The electrode-connector protecting cap as claimed in claim 10, wherein the wire fixing portion is of a protruded shape.

12. An electrode-connector for ambulatory physiological signal measurement, comprising:
    an electrode-connector having an electrode, a wire, a foam pad surrounding sides of the electrode, an electrode connecting portion taking one of a protruded shape and a recessed shape and electrically connected to the electrode, and a connector taking the other shape and electrically connected to the wire; and
    an electrode-connector protecting cap comprising:
    a hemisphere cap;
    a wind positioned at a periphery of the hemisphere cap and having a contact surface connected to the electrode-connector; and
    an opening for the wire to be passed through and formed in the hemisphere cap.

13. The electrode-connector as claimed in claim 12, wherein the hemisphere cap is formed by a transparent plastic.

14. The electrode-connector as claimed in claim 12, wherein the wing further comprises adhesive for connecting the wing to the electrode-connector.

15. The electrode-connector as claimed in claim 12, wherein the wing consists of three portions with 120° spaced from one another.

16. The electrode-connector as claimed in claim 12, wherein the wing is of a loop shape.

17. The electrode-connector as claimed in claim 12, wherein the wing has a groove.

18. The electrode-connector as claimed in claim 12, wherein the opening is positioned at the periphery of the hemisphere cap.

19. The electrode-connector as claimed in claim 12, further comprising a tube through which the wire is passed, and contacted around the opening of the hemisphere cap.

20. The electrode-connector as claimed in claim 19, wherein the tube is of an arch shape.

21. The electrode-connector as claimed in claim 19, wherein the tube has a wire fixing portion that can securely hold the wire.

22. The electrode-connector as claimed in claim 21, wherein the wire fixing portion is of a protruded shape.

* * * * *